(12) United States Patent
Nieskens et al.

(10) Patent No.: US 10,513,471 B2
(45) Date of Patent: Dec. 24, 2019

(54) PROCESSES AND SYSTEMS FOR ACHIEVING HIGH CARBON CONVERSION TO DESIRED PRODUCTS IN A HYBRID CATALYST SYSTEM

(71) Applicant: DOW GLOBAL TECHNOLOGIES LLC, Midland, MI (US)

(72) Inventors: Davy L. S. Nieskens, Terneuzen (NL); Aysegul Ciftci Sandikci, Terneuzen (NL); Peter E. Groenendijk, Terneuzen (NL); Barry B. Fish, Lake Jackson, TX (US); Andrzej M. Malek, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/461,693

(22) PCT Filed: Nov. 15, 2017

(86) PCT No.: PCT/US2017/061774
§ 371 (c)(1),
(2) Date: May 16, 2019

(87) PCT Pub. No.: WO2018/093880
PCT Pub. Date: May 24, 2018

(65) Prior Publication Data
US 2019/0352239 A1    Nov. 21, 2019

Related U.S. Application Data

(60) Provisional application No. 62/422,942, filed on Nov. 16, 2016.

(51) Int. Cl.
*C07C 1/06* (2006.01)
*C07C 1/04* (2006.01)
(Continued)

(52) U.S. Cl.
CPC .............. *C07C 1/06* (2013.01); *C01B 3/22* (2013.01); *C07C 1/043* (2013.01); *C07C 1/0485* (2013.01);
(Continued)

(58) Field of Classification Search
CPC ......... C07C 1/06; C07C 1/043; C07C 1/0485; C07C 9/06; C07C 9/14; C01B 3/22;
(Continued)

(56) References Cited

U.S. PATENT DOCUMENTS

2004/0127758 A1    7/2004   Van Egmond

FOREIGN PATENT DOCUMENTS

| WO | 0063141 A1 | 10/2000 |
| WO | 2005123883 A1 | 12/2005 |
| WO | 2016007607 A1 | 1/2016 |

OTHER PUBLICATIONS

International Search Report and Written Opinion pertaining to PCT/US2017/061774, dated Feb. 1, 2018.
(Continued)

*Primary Examiner* — Jafar F Parsa
(74) *Attorney, Agent, or Firm* — Dinsmore & Shohl LLP

(57) ABSTRACT

A process and system for preparing $C_2$ to $C_5$ hydrocarbons includes introducing a feed stream containing hydrogen gas and a carbon-containing gas selected from carbon monoxide, carbon dioxide, and mixtures thereof into a first reaction zone, contacting the feed stream and a hybrid catalyst in the first reaction zone, introducing a reaction zone product stream into a water removal zone that is downstream from the first reaction zone, and introducing a product stream from the water removal zone into a second reaction zone, resulting in a final stream comprising $C_2$ to $C_5$ hydrocarbons. The hybrid catalyst includes a methanol synthesis component and a microporous solid acid component; the micropo-
(Continued)

rous solid acid component is a molecular sieve having 8-MR access. The water removal zone removes at least a portion of water from the reaction zone product stream.

16 Claims, 5 Drawing Sheets

(51) Int. Cl.
    *C01B 3/22*    (2006.01)
    *C07C 9/08*    (2006.01)
    *C07C 9/10*    (2006.01)
    *C07C 9/14*    (2006.01)
    *C07C 9/06*    (2006.01)

(52) U.S. Cl.
    CPC .. *C01B 2203/061* (2013.01); *C01B 2203/062* (2013.01); *C07C 9/06* (2013.01); *C07C 9/08* (2013.01); *C07C 9/10* (2013.01); *C07C 9/14* (2013.01)

(58) Field of Classification Search
    CPC ........ C01B 2203/062; C01B 2203/061; C10G 2/00; C10G 2/32
    See application file for complete search history.

(56) References Cited

OTHER PUBLICATIONS

Calverley et al., "Kinetic Model for Alcohol Synthesis over a Promoted Cu/ZnO.Cr2O3 Catalyst", Ind. Eng. Chem. Res. 1992, 31, 792-803.
Joo et al., "Carbon Dioxide Hydrogenation to Form Methanol via a Reverse-Water-Gas-Shift Reaction (the CAMERE Process)", Ind. Eng. Chem. Res., 1999, 38 (5), pp. 1808-1812.
Fujimoto et al., "Selective Synthesis of C2-C5 Hydrocarbons From Carbon Dioxide Utilizing a Hybrid Catalyst Composed of a Methanol Synthesis Catalyst and Zeolite". Applied Catalysis, 1987, 13-23.
Lok et al., "Silicoaluminophosphate Molecular Sieves: Another New Class of Microporous Crystalline Inorganic Solids," J. Am. Chem. Soc. 106 (1984) 6092-6093.
Sierra et al., "Co-feeding Water to Attenuate Deactivation of the Catalyst Metallic Function (CuO—ZnO—Al2O3) by Coke in the Direct Synthesis of Dimethyl Ether", App Cat B 106 (2011), p. 167-173.
Tronconi et al., "Mechanistic Kinetic Treatment of the Chain Growth Process in High Alcohol Synthesis over a Cs-Promoted Zn—Cr—O Catalyst", Journal of Catalysis, 135, p. 99-114 (1992).
Vedage et al., "Water Promotion and Identification of Intermediates in Methanol Synthesis", Int. Congr. Catal., [Proc.], 8th, vol. 2, pp. II47-II58, Conference 1985 CODEN:55DBAG.

US 10,513,471 B2

PROCESSES AND SYSTEMS FOR ACHIEVING HIGH CARBON CONVERSION TO DESIRED PRODUCTS IN A HYBRID CATALYST SYSTEM

CROSS-REFERENCE TO RELATED APPLICATIONS

This application claims priority to U.S. Provisional Application Ser. No. 62/422,942 filed on Nov. 16, 2016, the entire disclosure of which is hereby incorporated by reference.

BACKGROUND

Field

The present specification generally relates to processes and systems for converting feed carbon to desired products while minimizing the conversion of the feed carbon to carbon dioxide ($CO_2$). In particular, the present specification relates to processes and systems that use a hybrid catalyst to achieve a high conversion of carbon contained in a synthesis gas feed stream, where the synthesis gas comprises hydrogen gas and a carbon-containing gas selected from the group consisting of carbon monoxide, carbon dioxide, and mixtures thereof, to desired products while minimizing the conversion of the feed carbon to $CO_2$.

Technical Background

For a number of industrial applications, a desirable starting material is a lower hydrocarbon, including in particular $C_2$ to $C_5$ olefins, and/or $C_2$ to $C_5$ paraffins that can then be converted to olefins, for use in or as starting materials to produce plastics, fuels, and various downstream chemicals. These $C_2$ to $C_5$ materials may be saturated or unsaturated and therefore may include ethane, ethylene, propane, and/or propylene. A variety of processes for producing these lower hydrocarbons has been developed, including petroleum cracking and various synthetic processes.

Synthetic processes for converting feed carbon to desired products, such as hydrocarbons, are known. Some of these synthetic processes begin with use of a hybrid catalyst. Different types of catalysts have also been explored, as well as different kinds of feed streams and proportions of feed stream components. However, many of these synthetic processes have low carbon conversion and much of the feed carbon does not get converted and exits the process in the same form as the feed carbon, or the feed carbon is converted to $CO_2$.

Accordingly, a need exists for processes and systems that have a high conversion of feed carbon to desired products, such as, for example, $C_2$ to $C_5$ hydrocarbons.

SUMMARY

According to one embodiment, a process for preparing $C_2$ to $C_5$ hydrocarbons comprises: introducing a feed stream comprising hydrogen gas and a carbon-containing gas selected from the group consisting of carbon monoxide, carbon dioxide, and mixtures thereof into a first reaction zone; contacting the feed stream and a hybrid catalyst in the first reaction zone, wherein the hybrid catalyst comprises a methanol synthesis component and a microporous solid acid component, wherein the microporous solid acid component is a molecular sieve having 8 membered ring (8-MR) access; introducing a reaction zone product stream into a water removal zone that is downstream from the first reaction zone, wherein the water removal zone removes at least a portion of water from the reaction zone product stream; and introducing a product stream from the water removal zone into a second reaction zone, resulting in a final stream comprising $C_2$ to $C_5$ hydrocarbons.

In another embodiment, a system for preparing $C_2$ to $C_5$ hydrocarbons comprises: a first reaction zone including a hybrid catalyst, the hybrid catalyst comprising a methanol synthesis component and a microporous solid acid component, wherein the microporous solid acid component is a molecular sieve having 8-MR access; a water removal zone downstream from the first reaction zone; and a second reaction zone that is downstream from the first reaction zone.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
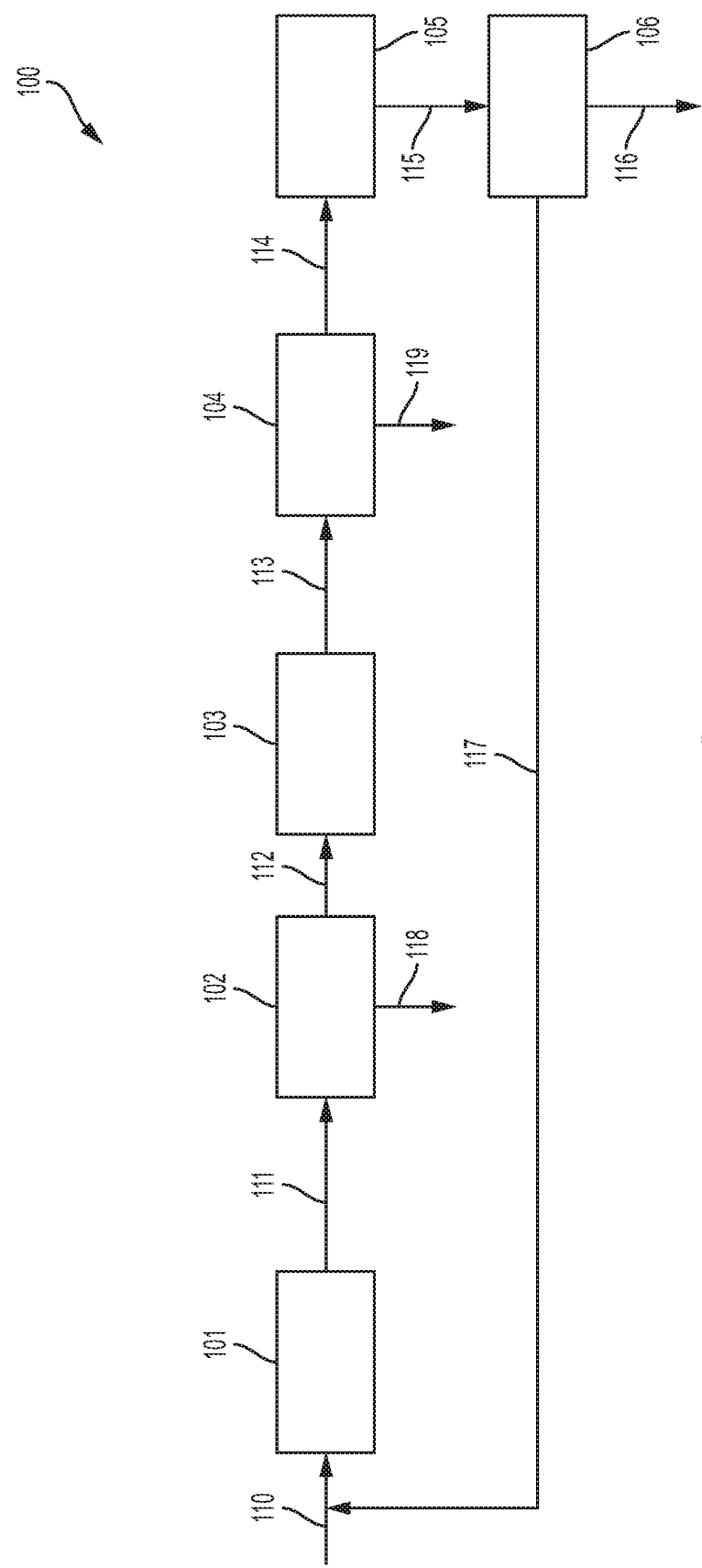
FIG. 1 is a block diagram flow chart for systems and processes of preparing $C_2$ to $C_5$ hydrocarbons according to embodiments disclosed and described herein.

Reference will now be made in detail to embodiments of processes and systems for preparing C2 to C5 hydrocarbons, embodiments of which are illustrated in the accompanying drawings. Whenever possible, the same reference numerals will be used throughout the drawings to refer to the same or like parts. In one embodiment, a process for preparing $C_2$ to $C_5$ hydrocarbons comprises: introducing a feed stream comprising hydrogen gas and a carbon-containing gas selected from the group consisting of carbon monoxide, carbon dioxide, and mixtures thereof into a first reaction zone; contacting the feed stream and a hybrid catalyst in the first reaction zone, wherein the hybrid catalyst comprises a methanol synthesis component and a microporous solid acid component, wherein the microporous solid acid component is a molecular sieve having 8-MR access; introducing a reaction zone product stream into a water removal zone that is downstream from the first reaction zone, wherein the water removal zone removes at least a portion of water from the reaction zone product stream; and introducing a product stream from the water removal zone into a second reaction zone, resulting in a final stream comprising $C_2$ to $C_5$ hydrocarbons. The methanol synthesis component can be a metal oxide catalyst, a mixed metal oxide catalyst, a supported metal oxide catalyst, or a supported mixed metal oxide catalyst capable of converting the feed stream into methanol or DME under hybrid process conditions. In some embodiments, the methanol synthesis component may be selected from the group consisting of a copper oxide catalyst, a copper oxide/zinc oxide catalyst, a copper oxide/alumina catalyst, a copper oxide/zinc oxide/alumina catalyst, a chromium oxide/zinc oxide catalyst, and combinations thereof. The microporous solid acid component can be a molecular sieve having 8-MR access.

The use of hybrid catalysts to convert feed streams comprising carbon to desired products, such as, for example, $C_2$ to $C_5$ hydrocarbons, is known. The composition of such hybrid catalysts used in embodiments is discussed below. In summary, hybrid catalysts closely couple sequential reactions on each of the two independent catalysts. In the first step, a feed stream, such as, for example, syngas, is converted into oxygenated hydrocarbons (mostly methanol and DME). In the second step, these oxygenates are converted into hydrocarbons (mostly short chain hydrocarbons, such as, for example $C_2$ to $C_5$ hydrocarbons). As used herein, the terms "hydrocarbon(s)" and "$C_2$ to $C_5$ hydrocarbons" refer to $C_2$ to $C_5$ hydrocarbons including, without limitation, $C_2$ to $C_5$ paraffins and $C_2$ to $C_5$ olefins. The continued withdrawal of oxygenates formed in the first step by the reactions of the second step ensure that there is no thermodynamic limit to achieve close to 100% (>99.9%) feed carbon conversion to hydrocarbons.

However, surprisingly, it has been found that water may negatively impact the maximum achievable feed carbon conversion to desired hydrocarbon products resulting in conversion significantly below the thermodynamic limit. This result is surprising, because in methanol synthesis, water originates from $CO_2$ which is co-fed with the CO and $H_2$ of the syngas stream. In other words, a stream consisting strictly of CO and $H_2$ (e.g., high-purity syngas) would have been thought to only yield methanol and no water. Therefore, any negative effects associated with water would not have been expected because, previously, water formation was not expected in the conversion of high-purity syngas. In addition, the hybrid catalyst process runs at very different process conditions compared to traditional methanol synthesis processes. Particularly, the temperature is much higher in the hybrid catalyst process. At the high temperature of the hybrid process, the maximum thermodynamic equilibrium yield of methanol is lower compared to the maximum yield under methanol synthesis conditions, which take place at a lower temperature. In view of this, it is surprising and unexpected that water would still have a negative, inhibiting effect under these conditions where the methanol equilibrium yield already is so low. Accordingly, at higher temperature it is expected that the adsorption of water on the catalyst surface is less (following well-known Langmuir adsorption characteristics) leading to the expectation that the formation of water will have little to no effect on the hybrid catalyst process.

Surprisingly, it has been found that known solutions in the syngas-to-products field dealing with the formation of $CO_2$ are not desirable for the hybrid catalyst system. In more generic syngas-to-products processes, there are basically two options for dealing with the formation of $CO_2$; purging $CO_2$, or recycling $CO_2$ "to extinction" back to a syngas reformer section or over a catalytic reactor. The first option (purging) leads to a significant carbon yield loss and is only feasible when the amount of $CO_2$ is very low, which is not the case for the hybrid catalyst process. It has also been found that the second option (recycling $CO_2$) is not desirable for the hybrid process for at least two reasons: it leads to a large and expensive separation section to separate $CO_2$ from the desired product; and it negatively impacts the catalyst productivity.

In view of the above problems, there is presently no way to deal with both the negative impact of water on achieving a high feed carbon conversion and the loss of feed carbon to $CO_2$. To address these problems, embodiments of processes and systems disclosed herein deal with both of the above problems by driving a reverse water-gas-shift reaction (R-WGS: $CO_2+H_2 \rightarrow CO+H_2O$) to near-completion while at the same time removing water from the product stream.

With reference now to FIG. 1, an embodiment of system for preparing $C_2$ to $C_5$ hydrocarbons from a carbon feed stream is provided. It should be understood that the embodiment depicted in FIG. 1 is exemplary and does not limit the scope of this disclosure. As shown in the embodiment of FIG. 1, splitting the overall reaction over several discrete reaction zones, including a water removal zone between the reaction zones. In embodiments, the number of zones can be adjusted based on the required overall conversion level. Thus, in embodiments, the reaction is allowed to proceed up to a certain point before water is removed.

The embodiment of a system for preparing $C_2$ to $C_5$ hydrocarbons 100 depicted in FIG. 1 includes three distinct reaction zones; a first reaction zone 101, a second reaction zone 103, and a third reaction zone 105. Between the first reaction zone 101 and the second reaction zone 103 is a first water removal zone 102. Between the second reaction zone 103 and the third reaction zone 105 is a second water removal zone 104. The reaction zones 101, 103, and 105 and the water removal zones 102 and 104 are fluidly connected to adjacent zones. For example, the first reaction zone 101 is fluidly connected to the first water removal zone 102, and the first water removal zone 102 is fluidly connected to the second reaction zone 103, etc. The final reaction zone 105 in the system 100 is fluidly connected to a separator 106 that separates a product stream 116 from a recycling stream 117. As shown in FIG. 1, a water removal zone is positioned downstream from and fluidly connected to each reaction zone, with the exception of the final reaction zone in the system, which is fluidly connected to a separator.

It should be understood that although the embodiment of FIG. 1 includes three reaction zones and two water removal zones, in other embodiments any number of reaction zones may be used in the system to achieve the required conversion of the carbon feed stream to products, and the number of water removal zones in such embodiments may be one less than the number of reaction zones. Thus, in some embodiments, the number of reaction zones (n) is determined by the required conversion of the carbon feed stream and the number of water removal zones is one less (n−1) than the number of reaction zones. However, in other embodiments not depicted, a water removal zone may be positioned downstream from and fluidly connected to the final reaction zone so that the number of reaction zones is equal to the number of water removal zones. In the embodiment depicted in FIG. 1, such an embodiment would include a third water removal zone (not shown) positioned between and fluidly connected to the third reaction zone 105 and the separator 106. In still other embodiments, multiple reaction zones may be adjacent to and fluidly connected with one another, and these multiple reaction zones may be fluidly connected to a downstream water removal zone, such that the number of water removal zones is less than n−1, such as n−2, n−3, etc.

In one or more embodiments, each reaction zone 101, 103, and 105 may be a hybrid reactor that comprises a hybrid catalyst. The hybrid catalyst may include: (1) a methanol synthesis component; and (2) a solid microporous acid component having 8-MR access. In some embodiments, the methanol synthesis component is selected from the group consisting of a copper oxide catalyst, a copper oxide/zinc oxide catalyst, a copper oxide/alumina catalyst, a copper oxide/zinc oxide/alumina catalyst, a chromium oxide/zinc oxide catalyst, and combinations thereof. In embodiments, the solid microporous acid component is selected from molecular sieves having 8-MR access and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the molecular sieve may be SAPO-34 silicoaluminophosphate having a CHA framework type.

In other embodiments, the water removal zones 102 and 104 may include any suitable reaction or process for removing water from a gas stream, such as, for example, condensing by cooling, using a membrane that separates water from the gas stream, or adding a water absorbent to remove water from the gas stream. By removing water from the gas stream between each reaction zone, the carbon feed stream going into subsequent reaction zones is essentially water free, which permits higher conversion of the carbon in the carbon feed stream to desired products, such as $C_2$ to $C_5$ hydrocarbons. In some embodiments, the water may be removed from a gas stream by cooling the gas stream while the gas stream is at a temperature up to 120° C., such as from greater than or equal to 20° C. to less than or equal to 75° C., or from greater than or equal to 30° C. to less than or equal to 60° C., and the gas stream is at pressures from greater than or equal to 10 bar (1000 kPa) to less than or equal to 100 bar (10000 kPa), such as from greater than or equal to 25 bar (2500 kPa) to less than or equal to 75 bar (7500 kPa), or from greater than or equal to 35 bar (3500 kPa) to less than or equal to 65 bar (6500 kPa).

In further embodiments, any suitable reaction or process for separating the desired product from the other components in the feed stream may be used in the separator 106. It should be understood that in some embodiments, the separator 106 may comprise only one separation process, but in other embodiments, the separator 106 may include a plurality of separation processes. In embodiments, the separation processes that may occur in the separator 106 include: (1) bulk removal of water using condensation at low temperatures (such as the processes discussed above for the water removal zones); (2) $CO_2$ removal using a chemical adsorption system, such as, for example, a methylamine in water system that operates at temperatures from greater than or equal to 25° C. to less than or equal to 65° C., such as from greater than or equal to 35° C. to less than or equal to 55° C. and operates at pressures from greater than or equal to 8 bar (800 kPa) to less than or equal to 50 bar (5000 kPa), such as from greater than or equal to 15 bar (1500 kPa) to less than or equal to 35 bar (3500 kPa); (3) trace removal of water using a 3A molecular sieve at ambient temperature, such as from greater than or equal to 5° C. to less than or equal to 50° C., or from greater than or equal to 15° C. to less than or equal to 25° C. and pressures from greater than or equal to 8 bar (800 kPa) to less than or equal to 50 bar (5000 kPa), such as from greater than or equal to 15 bar (1500 kPa) to less than or equal to 35 bar (3500 kPa); (4) cryogenic separation of non-condensable gasses such as $H_2$ and $N_2$; (5) distillation to remove CO and methane from the product stream, the distillation operating with temperatures at the top of the column of −90° C., and temperatures at the bottom of the column at 45° C. and operating at pressures of 30 bar (3000 kPa). It should be understood that in embodiments these separation processes may be duplicated any number of times in the separator 106 and can be used in any combination.

It was discovered that splitting a certain hybrid catalyst amount over multiple reaction zones in series with intermediate removal of water from the gas stream between the reaction zones enables both a higher $CO_x$ conversion as well as a higher $C_2$ to $C_5$ hydrocarbon productivity when compared to using this same amount of catalyst in a single reaction zone. Alternatively, a lower amount of catalyst in total can be used in the staged reaction zones to achieve similar $CO_x$ conversion, but at a much higher $C_2$ to $C_5$ hydrocarbon productivity compared to a higher amount of catalyst in a single, physical reaction zone. As used herein, $CO_x$ refers to carbon oxides where x=1 or 2.

In embodiments, the reaction zones 101, 103, and 105 and the water removal zones 102 and 104 may be distinct zones in a single reactor. However, in other embodiments, the reaction zones 101, 103, and 105 and the water removal zones 102 and 104 may be physically separate units.

Embodiments of processes for preparing $C_2$ to $C_5$ hydrocarbons will now be described with reference to FIG. 1. A feed stream 110 is fed into the first reaction zone 101, the feed stream comprising hydrogen ($H_2$) gas and a carbon-containing gas selected from carbon monoxide (CO), carbon dioxide ($CO_2$), and combinations thereof. In some embodiments, the $H_2$ gas is present in the feed stream 110 in an amount of from 10 volume percent (vol %) to 90 vol %, based on combined volumes of the $H_2$ gas and the gas selected from CO, $CO_2$, and combinations thereof. In some embodiments $H_2$ is present in the feed stream 110 in an amount from 20 vol % to 80 vol %, such as from 30 vol % to 70 vol %, or 40 vol % to 60 vol %. The feed stream 110 is contacted with a hybrid catalyst in the first reaction zone 101. The hybrid catalyst comprises: (1) a methanol synthesis component; and (2) a solid microporous acid component having 8-MR access. In some embodiments, the methanol synthesis component is selected from the group consisting of a copper oxide catalyst, a copper oxide/zinc oxide catalyst, a copper oxide/alumina catalyst, a copper oxide/zinc oxide/alumina catalyst, a chromium oxide/zinc oxide catalyst, and combinations thereof. In embodiments, the solid microporous acid component is selected from molecular sieves having 8-MR access to limit the size distribution of products and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the molecular sieve may be SAPO-34 silicoaluminophosphate having a CHA framework type. The feed stream 110 is contacted with the hybrid catalyst in the first reaction zone 101 under reaction conditions sufficient to form a first reaction zone product stream 111. The reaction conditions may comprise: a temperature ranging from 300 degrees Celsius (° C.) to 440° C., such as from 350° C. to 400° C., or from 365° C. to 385° C.; a pressure of at least 1 bar (100 kilopascals, kPa), such as at least 2 bar (200 kPa), or at least 3 bar (300 kPa); and a gas hourly space velocity (GHSV) of at least 500 reciprocal hours ($h^{-1}$), such as at least 550 $h^{-1}$, or at least 600 $h^{-1}$. The first reaction zone product stream comprises CO, $H_2$, $CO_2$, water, and hydrocarbons.

The above process has utility in that it converts a feed stream 110 that comprises, consists essentially of or consists of $H_2$ gas and a gas selected from CO, $CO_2$, or a combination thereof, to a first reaction zone product stream 111 that comprises a combination of saturated and unsaturated $C_2$ to $C_5$ hydrocarbons. The first reaction zone product stream 111 itself has utility as a cracker feed stream to produce certain olefins and/or as a starting material or intermediate to produce a range of chemical products including plastics, fuels and the like.

It will be understood that CO or $CO_2$ may each be present in the feed stream 110 as a sole second gas, or a combination of both may be present, in any proportion relative to one another. In other words, in one or more embodiments, the feed stream may comprise, consist essentially of, or consist of, (1) a combination of CO and $H_2$, or (2) a combination of $CO_2$ and $H_2$, or (3) a combination of (1) and (2) (such being a combination of CO, $CO_2$, and $H_2$), and regardless of which embodiment is employed, such will react according to the process conditions of the reaction zone 101 to form a combination of saturated and unsaturated $C_2$ to $C_5$ products. In embodiments, the first reaction zone product stream may contain CO, $CO_2$, and $H_2$ originating from either unconverted feed components, the Water Gas Shift reaction (WGS), or the reverse WGS.

Those skilled in the art will be able, with minimal experimentation, to ascertain the desired balance between feed stream 110 composition and desired $C_2$ to $C_5$ hydrocarbons and proportions thereof, as will be described further herein below.

Where more than 50 mole-percent (mol %) of all carbon in the feed stream 110 is initially in the form of CO, the CO may be said to be the primary carbon-containing constituent of the feed stream. In embodiments, such CO is present in an amount greater than 60 mol %, such as greater than 70 mol %, greater than 80 mol %, and greater than 90 mol %. $H_2$ gas is separately measured and is desirably present in the feed stream in a volumetric ratio of $H_2$ to CO ($H_2$:CO) that is greater than or equal to 0.5:1, such as greater than or equal to 0.6:1, greater than or equal to 1:1, greater than or equal to 2:1. In embodiments, $H_2$:CO is less than or equal to 10:1, such as less than or equal to 7:1. In some embodiments, $H_2$:CO is greater than or equal to 3:1 to less than or equal to 6:1.

Where more than 50 mol % of all carbon in the feed stream 110 is initially in the form of $CO_2$, the $CO_2$ may be said to be the primary carbon-containing constituent of the feed stream. In embodiments, such $CO_2$ is present in an amount greater than 60 mol %, such as greater than 70 mol %, greater than 80 mol %, and greater than 90 mol %. $H_2$ gas is separately measured and is, in embodiments, present in the feed stream 110 in a volumetric ratio of $H_2$ to $CO_2$ ($H_2$:$CO_2$) that is greater than or equal to 0.5:1, such as greater than or equal to 0.6:1, greater than or equal to 1:1, greater than or equal to 2:1. In embodiments $H_2$:$CO_2$ is less than or equal to 10:1, such as less than or equal to 9:1. In some embodiments, $H_2$:$CO_2$ is greater than or equal to 3:1 to less than or equal to 8:1.

In embodiments, the feed stream 110 is passed into a reaction zone via a heated reactor inlet, and in the reactor the feed stream 110 typically moves over and/or through a hybrid catalyst bed under conditions sufficient to convert the carbon-containing gas (CO, $CO_2$, or a combination thereof) into the first reaction zone product stream. The conditions under which this process may be carried out comprise, consist essentially of, or consist of: (1) a temperature ranging from 300 degrees ° C. to 440° C., such as from 350° C. to 400° C., or from 365° C. to 385° C.; (2) a pressure of at least 1 bar (100 kPa), such as at least 2 bar (200 kPa), or at least 3 bar (300 kPa); and (3) a GHSV of at least 500 $h^{-1}$, such as at least 550 $h^{-1}$, or at least 600 $h^{-1}$. As used herein, the phrase "reactor temperature" will be understood to represent either an average reactor temperature, where temperature is measured at more than one location within the reactor, or the sole temperature, where temperature is measured at only one location within the reactor. However, those skilled in the art will recognize that the temperature at different locations within the reactor will almost certainly vary somewhat, according to flow rates, catalyst flow and bed packing, reactor size and geometry, variation in reactor inlet temperatures, and so forth, and will be able to easily adjust process parameters and other means to control temperature, such as the use of a multi-tube heat exchanger, to ensure that the reactor temperature requirements of the present invention are met.

In certain embodiments, where the primary carbon-containing constituent of the feed stream 110, as defined hereinabove, is CO, such reaction conditions comprise, consist essentially of, or consist of: (1) a reactor temperature ranging from 350° C., such as from 360° C., or from 370° C., to 440° C., such as to 410° C., and to 390° C.; (2) a pressure of at least 1 bar (100 kPa), such as at least 2 bar (200 kPa), or at least 3 bar (300 kPa); and (3) a GHSV from 500 $h^{-1}$, such as from 1000 $h^{-1}$, from 3000 $h^{-1}$, to 12000 $h^{-1}$, to 10000 $h^{-1}$, and to 6000 $h^{-1}$.

In other embodiments, where the feed stream comprises carbon that is predominantly, as defined hereinabove, in the form of $CO_2$, such reaction conditions comprise, consist essentially of, or consist of: (1) a reactor temperature ranging from 300° C., such as from 320° C., and from 330° C., to 400° C., such as to 390° C., and to 380° C.; (2) a pressure of at least 1 bar (100 kPa), such as at least 2 bar (200 kPa), or at least 3 bar (300 kPa); and (3) a GHSV from 500 $h^{-1}$, such as from 1000 $h^{-1}$, and from 3000 $h^{-1}$, to 22000 $h^{-1}$, such as to 10000 $h^{-1}$, and to 6000 $h^{-1}$.

The hybrid catalyst bed comprises, consists of, or consists essentially of (1) a methanol synthesis component; and (2) a solid microporous acid component having 8-MR access. In some embodiments, the methanol synthesis component is selected from the group consisting of a copper oxide catalyst, a copper oxide/zinc oxide catalyst, a copper oxide/alumina catalyst, a copper oxide/zinc oxide/alumina catalyst, a chromium oxide/zinc oxide catalyst, and combinations thereof. In embodiments, the solid microporous acid component is selected from molecular sieves having 8-MR access to limit the size distribution of products and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the molecular sieve may be SAPO-34 silicoaluminophosphate having a CHA framework type. Examples of these may include, but are not necessarily limited to: CHA embodiments selected from SAPO-34 and SSZ-13; and AEI embodiments such as SAPO-18. As the term is used herein, "SAPO" molecular sieves are defined as silicoaluminophosphate materials having a silicon content of at least 0.01 wt %, such as at least 0.1 wt %, and at least 0.5 wt %. Many of these materials will have a silicon content of at least 5 wt % or greater. Thus, based upon this definition, molecular sieves that are primarily aluminophosphates, but actually contain very minor amounts of silicon (i.e., less than 0.01 wt %, would still be classified as "ALPO" molecular sieves). Combinations of molecular sieves having any of the above framework types may also be employed. It should be understood that the solid microporous acid component may have different membered ring access depending on the desired product. For instance, solid microporous acid components having 8-MR to 12-MR access could be used depending on the desired product. However, to produce $C_2$ to $C_5$ hydrocarbons, solid microporous acid components having 8-MR access are used in embodiments.

In embodiments, the selected molecular sieve is non-metal-modified (i.e., it does not include in its crystal lattice any metal heteroatoms beyond those of which the lattice as a whole is composed). Thus, for example only, a silicoaluminate (e.g., a zeolite such as Beta) would not include any metal atom other than silicon and aluminum, and a silicoaluminophosphate, such as a SAPO, would not include any metal atom other than silicon, aluminum, and phosphorus.

With regard to specifically the SAPO silicoaluminophosphate molecular sieves, it will be understood by those skilled in the art that the elemental composition of the anhydrous form may be represented as $(Si_xAl_yP_z)O_2$, where x, y and z represent molar fractions of silicon, aluminum and phosphorus, with x+y+z=1. See, for example, Lok, B. M., et al., "Silicoaluminophosphate Molecular Sieves: Another New Class of Microporous Crystalline Inorganic Solids," J. Am. Chem. Soc. 106 (1984) 6092-6093.

As noted above, use of a combination of these methanol synthesis components in admixture with a molecular sieve is also acceptable, and the methanol synthesis component may be made separately or together. The methanol synthesis component and the molecular sieve catalyst may be present in the reactor, typically as a mixed catalyst in a catalyst bed, in a weight/weight (wt/wt) ratio (methanol synthesis component:molecular sieve catalyst) ranging from 0.1:1 to 10:1, such as from 0.5:1 to 9:1.

In embodiments, the methanol synthesis component may comprise one or more of the elements Cu, Zn, Cr, and Al, in any possible compositional combination and in either metallic or oxidic form.

It is additionally noted that the aluminum oxide (i.e., alumina) may be in any phase or combination of phases. However, in some embodiments a gamma-alumina, or predominantly (more than 50 wt %) of gamma-alumina, the weight percent being based on total alumina may be used. Other phases of aluminas, such as alpha-alumina, omega-alumina, eta-alumina, etc., may be used alternatively or as a component, such as a minor component, with another alumina phase, such as a gamma phase.

The product mixture resulting from the inventive process, following contact between the feed stream and the mixed catalyst under the specified reaction conditions, may desirably be high in saturated and unsaturated $C_2$ to $C_5$ products, such as ethane, and/or propane, and/or ethylene and/or propylene; relatively low in $C_1$ products, such as $CH_4$; and relatively low in oxygenated products.

In addition to the above hydrocarbons, the first reaction zone product stream 111 will contain some proportion of unconverted gas selected from $H_2$, CO, $CO_2$, and combinations thereof, depending upon feed stream composition and water. The amount of each will vary according to a variety of factors well known to those skilled in the art, including carbon conversion, yield, catalyst productivity, time on stream, and so forth.

The first reaction zone product stream 111 is then introduced into the first water removal zone 102. In the first water removal zone 102, at least a portion of the water in the first reaction zone product stream 111 is removed and discarded as water stream 118. The water may be removed from the first reaction zone product stream 111 by any suitable process, such as condensation by cooling, using a membrane that separates the water from the remainder of the first reaction zone product stream 111, or by adding an absorbent to the first reaction zone product stream 111. Processing conditions of the water removal zone are discussed above. Removal of the water produces a first water removal zone product stream 112 that comprises $H_2$, CO, $CO_2$, and hydrocarbons. The hydrocarbons from the first reaction zone product stream 111 essentially pass through the first water removal zone 102, thus the hydrocarbons in the first water removal zone product stream 112 may comprise the same hydrocarbon components as outlined above for the first reaction zone product stream 111.

Subsequently, the first water removal zone product stream 112 is introduced into the second reaction zone 103. The second reaction zone 103 comprises a hybrid catalyst as described above for the first reaction zone. Namely, the hybrid catalyst in the second reaction zone 103 comprises: (1) a methanol synthesis component; and (2) a solid microporous acid component having 8-MR access. In some embodiments, the methanol synthesis component is selected from the group consisting of a copper oxide catalyst, a copper oxide/zinc oxide catalyst, a copper oxide/alumina catalyst, a copper oxide/zinc oxide/alumina catalyst, a chromium oxide/zinc oxide catalyst, and combinations thereof. In embodiments, the solid microporous acid component is selected from molecular sieves having 8-MR access to limit the size distribution of products and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the molecular sieve may be SAPO-34 silicoaluminophosphate having a CHA framework type. It should be understood that the hybrid catalyst in the second reaction zone 103 may be the same or different from the hybrid catalyst in the first reaction zone 101. When the first water removal zone product stream 112 is introduced into the second reaction zone 103, the reverse water-gas shift reaction takes place where the $CO_2$ and the $H_2$ in the first water removal zone product stream 112 is reacted to form CO and water. Before, after, or concurrent to this reaction, CO and $H_2$ in the first water removal zone product stream 112 is reacted to form hydrocarbons. However, not all of the $CO_2$ introduced to the second reaction zone 103 is converted into CO and water.

Thus, the produced second reaction zone product stream 113 comprises CO, $H_2$, $CO_2$, water, and hydrocarbons. It should be understood that the reactions and process discussed above that take place in the first reaction zone 101 also take place in the second reaction zone 103.

The second reaction zone product stream 113 is then introduced into the second water removal zone 104. In the second water removal zone 104, at least a portion of the water in the second reaction zone product stream 113 is removed and discarded as water stream 119. The water may be removed from the second reaction zone product stream 113 by any suitable process, such as condensation by cooling, using a membrane that separates the water from the remainder of the second reaction zone product stream 113, or by adding an absorbent to the second reaction zone product stream 113. Processing conditions of the water removal zone are discussed above. Removal of the water produces a second water removal zone product stream 114 that comprises $H_2$, CO, $CO_2$, and hydrocarbons. The hydrocarbons from the second reaction zone product stream 113 essentially pass through the second water removal zone 104, thus the hydrocarbons in the second water removal zone product stream 114 may comprise the same hydrocarbon components as outlined above for the first and second reaction zone product streams 111 and 113.

Subsequently, the second water removal zone product stream 114 is introduced into the third reaction zone 105. The third reaction zone 105 comprises a hybrid catalyst as described above for the first and second reaction zones. Namely, the hybrid catalyst in the third reaction zone 105 comprises: (1) a methanol synthesis component; and (2) a solid microporous acid component having 8-MR access. In some embodiments, the methanol synthesis component is selected from the group consisting of a copper oxide catalyst, a copper oxide/zinc oxide catalyst, a copper oxide/alumina catalyst, a copper oxide/zinc oxide/alumina catalyst, a chromium oxide/zinc oxide catalyst, and combinations thereof. In embodiments, the solid microporous acid component is selected from molecular sieves having 8-MR access to limit the size distribution of products and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the molecular sieve may be SAPO-34 silicoaluminophosphate having a CHA framework type. It should be understood that the hybrid catalyst in the third reaction zone 105 may be the same or different from the hybrid catalyst in the first and second reaction zones 101 and 103. When the second water removal zone product stream 114 is introduced into the third reaction zone 105, the reverse water-gas shift reaction takes place where the $CO_2$ and the $H_2$ in the second water removal zone product stream 114 is reacted to form CO and water. Before, after, or concurrent to this reaction, CO and $H_2$ in the second water removal zone product stream 114 is reacted to form hydrocarbons. By this point, essentially all of the $CO_2$ introduced to the third reaction zone 105 is converted into CO and hydrocarbons. Thus, the produced third reaction zone product stream 115 comprises mostly CO, $H_2$, and hydrocarbons. However, some water and $CO_2$ may be present in the third reaction zone product stream in very small amounts as contaminants. It should be understood that the reactions and process discussed above that take place in the first reaction zone 101 also take place in the second reaction zone 103 and in the third reaction zone 105.

As stated above, in some embodiments, the third reaction zone product stream 115 may be introduced into a third water removal zone (not shown) to remove any residual water from the third reaction zone product stream 115 before it is introduced to the separator 106. The third water removal zone, if used, functions in an identical manner as the first and second water removal zones 102 and 104 described above. It should be understood that the process for removing water from the third reaction zone product stream 115 in the third water removal zone may be the same or different from the process for removing water used in either the first or second water removal zones 102 and 104.

In the embodiment depicted in FIG. 1, the third reaction zone product stream 115 is introduced to a separator 106 where the desired product, such as, for example, $C_2$ to $C_5$ hydrocarbons are separated from the remainder of the components in the third reaction zone product stream 115. The isolated, desired product is removed from the separator 106 as a first product stream 116 comprising hydrocarbons. The remainder of the components of the third reaction zone product stream 115 (e.g., $H_2$ and CO) is removed from the separator 106 as a second product stream 117 and combined with the feed stream 110. In embodiments, the separator 106 is a cryogenic separator that cools the third reaction zone product stream 115 to a mixture of gas and liquid where the liquid is the first product stream and the gas is the second product stream. Further treatment of the liquid product stream to remove dissolved impurities such as $H_2$, CO, and methane through a distillation step may be desired. Separation processes and conditions of the separator are discussed above. It should be understood that any suitable separation process may be used to separate the desired product, such as $C_2$ to $C_5$ hydrocarbons, from the remainder of the components in the third reaction zone product stream 115.

It should be understood that in the embodiment depicted in FIG. 1, a heater or cooler may optionally be placed before any of the reaction zones or water removal zones to heat or cool the streams entering any of the reaction zones or water removal zones to the desired temperature for the processes taking place in the reaction zones or water removal zones. The type of heater or cooler used is not limited so long as it is capable of heating or cooling the incoming product stream to the desired process temperature.

Additional systems and processes for preparing $C_2$ to $C_5$ hydrocarbons according to embodiments will now be described with reference to FIG. 2. The embodiment of a system for preparing $C_2$ to $C_5$ hydrocarbons 200 depicted in FIG. 2 includes at least two distinct reaction zones; a first reaction zone 201 and a second reaction zone 203. Between the first reaction zone 201 and the second reaction zone 203 is a first water removal zone 202. The reaction zones 201 and 203 and the water removal zones 202 and 204 are fluidly connected to adjacent zones. For example, the first reaction zone 201 is fluidly connected to the first water removal zone 202, and the first water removal zone 202 is fluidly connected to the second reaction zone 203. The second reaction zone 203 is fluidly connected to a second water removal zone 204. The second water removal zone 204 is fluidly connected to a separator 205. The separator 205 is fluidly connected to the first reaction zone 201 and the second reaction zone 203. The separator separates the desired product from the other components of an input stream, thereby isolating the desired product and providing the other components as a recycle stream.

In embodiments, the first reaction zone 201 may be a hybrid reactor that comprises a hybrid catalyst. The hybrid catalyst may include: (1) a methanol synthesis component; and (2) a solid microporous acid component having 8-MR access. In some embodiments, the methanol synthesis component is selected from the group consisting of a copper oxide catalyst, a copper oxide/zinc oxide catalyst, a copper oxide/alumina catalyst, a copper oxide/zinc oxide/alumina catalyst, a chromium oxide/zinc oxide catalyst, and combinations thereof. In embodiments, the solid microporous acid component is selected from molecular sieves having 8-MR access to limit the size distribution of products and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the molecular sieve may be SAPO-34 silicoaluminophosphate having a CHA framework type. It should be understood that the hybrid reactor of the first reaction zone 201 may be the same as the hybrid reactors described above with reference to the embodiment of FIG. 1.

In further embodiments, the water removal zone 202 may include any suitable reaction or process for removing water from a gas stream, such as, for example, condensing by cooling, using a membrane that separates water from the gas stream, or adding a water absorbent to remove water from the gas stream. By removing water from the gas stream between each reaction zone, the carbon feed stream going into subsequent reaction zones is essentially water free, which permits higher conversion of the carbon in the carbon feed stream to desired products, such as $C_2$ to $C_5$ hydrocarbons. It should be understood that the water removal zone 202 may be the same as the water removal zones described above with reference to the embodiment of FIG. 1.

Referring again to FIG. 2, the second reaction zone 203 may include a reverse water-gas shift (R-WGS) reactor. In the R-WGS reactor, $CO_2$ and $H_2$ from a feed stream are converted to CO and water. The second reactor zone operates at temperatures from greater than or equal to 200° C. to less than or equal to 750° C., from greater than or equal to 300° C. to less than or equal to 650° C., or about 380° C., and pressures from greater than or equal to 10 bar (1000 kPa) to less than or equal to 100 bar (10000 kPa), such as from greater than or equal to 25 bar (2500 kPa) to less than or equal to 75 bar (7500 kPa), or from greater than or equal to 35 bar (3500 kPa) to less than or equal to 65 bar (6500 kPa).

In other embodiments, the second water removal zone 204 may include any suitable reaction or process for removing water from a gas stream, such as, for example, condensing by cooling, using a membrane that separates water from the gas stream, or adding a water absorbent to remove water from the gas stream. By removing water from the gas stream between each reaction zone, the carbon feed stream going into subsequent reaction zones is essentially water free, which permits higher conversion of the carbon in the carbon feed stream to desired products, such as $C_2$ to $C_5$ hydrocarbons or conversion of $CO_2$ and $H_2$ to CO and water. It should be understood that the water removal zone 204 may be the same as the first water removal zone 202 discussed above and/or the water removal zones described above with reference to the embodiment of FIG. 1.

In additional embodiments, any suitable reaction or process for separating the desired product from the other components in the feed stream may be used in the separator 205. It should be understood that in some embodiments, the separator 205 may comprise only one separation process, but in other embodiments, the separator 205 may include a plurality of separation processes. In embodiments, the separation processes that may occur in the separator 205 include: (1) bulk removal of water using condensation at low temperatures (such as the processes discussed above for the water removal zones); (2) $CO_2$ removal using a chemical adsorption system, such as, for example, a methylamine in water system that operates at temperatures from greater than or equal to 25° C. to less than or equal to 65° C., such as from greater than or equal to 35° C. to less than or equal to 55° C. and operates at pressures from greater than or equal to 8 bar (800 kPa) to less than or equal to 50 bar (5000 kPa), such as from greater than or equal to 15 bar (1500 kPa) to less than or equal to 35 bar (3500 kPa); (3) trace removal of water using a 3A molecular sieve at ambient temperature, such as from greater than or equal to 5° C. to less than or equal to 50° C., or from greater than or equal to 15° C. to less than or equal to 25° C. and pressures from greater than or equal to 8 bar (800 kPa) to less than or equal to 50 bar (5000 kPa), such as from greater than or equal to 15 bar (1500 kPa) to less than or equal to 35 bar (3500 kPa); (4) cryogenic separation of non-condensable gasses such as $H_2$ and $N_2$; (5) distillation to remove CO and methane from the product stream, the distillation operating with temperatures at the top of the column of −90° C., and temperatures at the bottom of the column at 45° C. and operating at pressures of 30 bar (3000 kPa). It should be understood that in embodiments these separation processes may be duplicated any number of times in the separator 205 and can be used in any combination. It should be understood that any suitable reaction or process for separating the desired product from the other components in the feed stream may be used. It should be understood that separator 205 may be the same as separator described above with reference to the embodiment of FIG. 1.

Embodiments of processes for preparing $C_2$ to $C_5$ hydrocarbons will now be described with reference to FIG. 2. A feed stream 210 is fed into the first reaction zone 201, the feed stream comprising $H_2$ and a carbon-containing gas selected from CO, $CO_2$, and combinations thereof. In some embodiments, the $H_2$ gas is present in the feed stream 210 in an amount of from 10 volume percent (vol %) to 90 vol %, based on combined volumes of the $H_2$ gas and the gas selected from CO, $CO_2$, and combinations thereof. The feed stream 210 is contacted with a hybrid catalyst in the first reaction zone 201. The hybrid catalyst comprises: (1) a methanol synthesis component; and (2) a solid microporous acid component having 8-MR access. In some embodiments, the methanol synthesis component is selected from the group consisting of a copper oxide catalyst, a copper oxide/zinc oxide catalyst, a copper oxide/alumina catalyst, a copper oxide/zinc oxide/alumina catalyst, a chromium oxide/zinc oxide catalyst, and combinations thereof. In embodiments, the solid microporous acid component is selected from molecular sieves having 8-MR access to limit the size distribution of products and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the molecular sieve may be SAPO-34 silicoaluminophosphate having a CHA framework type. The feed stream 210 is contacted with the hybrid catalyst in the first reaction zone 201 under reaction conditions sufficient to form a first reaction zone product stream 211. The reaction conditions comprising: (1) a temperature ranging from 300 degrees ° C. to 440° C., such as from 350° C. to 400° C., or from 365° C. to 385° C.; (2) a pressure of at least 1 bar (100 kPa), such as at least 2 bar (200 kPa), or at least 3 bar (300 kPa); and (3) a GHSV of at least 500 h$^{-1}$, such as at least 550 h$^{-1}$, or at least 600 h$^{-1}$. The first reaction zone product stream comprises CO, H$_2$, CO$_2$, water, and hydrocarbons. The first reaction zone 201 functions in the same manner as reaction zones 101, 103, and 105 discussed above, thus the function of the first reaction zone and the product stream produced thereby is not discussed in such detail here.

The first reaction zone product stream 211 is then introduced into the first water removal zone 202. In the first water removal zone 202, at least a portion of the water in the first reaction zone product stream 211 is removed and discarded as water stream 217. The water may be removed from the first reaction zone product stream 211 by any suitable process, such as condensation by cooling, using a membrane that separates the water from the remainder of the first reaction zone product stream 211, or by adding an absorbent to the first reaction zone product stream 211. Processing conditions of the first water removal zone are discussed above. Removal of the water produces a first water removal zone product stream 212 that comprises H$_2$, CO, CO$_2$, and hydrocarbons. The hydrocarbons from the first reaction zone product stream 211 essentially pass through the first water removal zone 202, thus the hydrocarbons in the first water removal zone product stream 212 may comprise the same hydrocarbon components as outlined above for the first reaction zone product stream 211.

Figure 2:
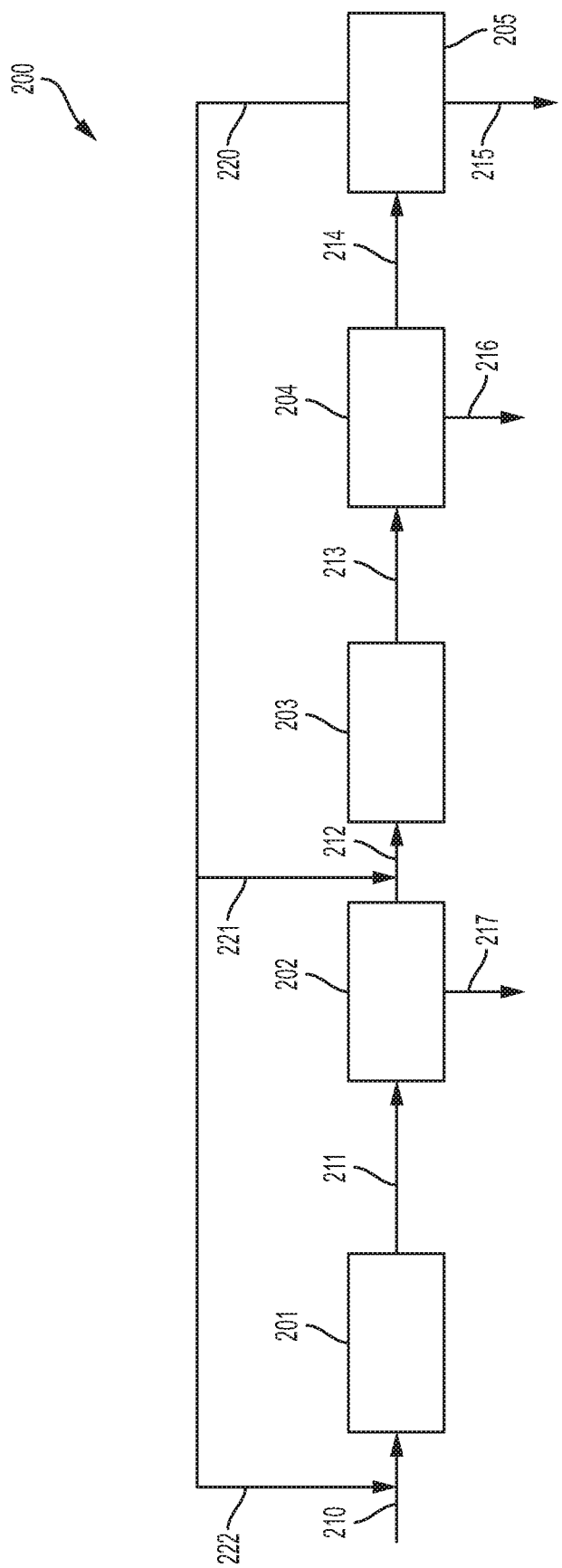
FIG. 2 is a block diagram flow chart for systems and processes of preparing $C_2$ to $C_5$ hydrocarbons according to embodiments disclosed and described herein.

Further, as shown in FIG. 2, the first water removal zone product stream 212 is then introduced into the second reaction zone 203. In embodiments, the second reaction zone 203 is an R-WGS reactor where the CO$_2$ and H$_2$ in the first water removal zone product stream 212 is converted to CO and water. The operating conditions of the second reaction zone 203 are provided above. The conversion in the second reaction zone 203 provides a second reaction zone product stream 213 that comprises CO, H$_2$, CO$_2$, water, and hydrocarbons, such as C$_2$ to C$_5$ hydrocarbons. This conversion of CO$_2$ into CO provides more feed CO that can be used to form hydrocarbons.

The second reaction zone product stream 213 is introduced to the second water removal zone 204. In the second water removal zone 204, at least a portion of the water in the second reaction zone product stream 213 is removed and discarded as water stream 216. The water may be removed from the second reaction zone product stream 213 by any suitable process, such as condensation by cooling, using a membrane that separates the water from the remainder of the second reaction zone product stream 213, or by adding an absorbent to the second reaction zone product stream 213. Processing conditions of the water removal zone are discussed above. Removal of the water produces a second water removal zone product stream 214 that comprises H$_2$, CO, CO$_2$, and hydrocarbons. The hydrocarbons from the second reaction zone product stream 213 essentially pass through the second water removal zone 204, thus the hydrocarbons in the second water removal zone product stream 214 may comprise the same hydrocarbon components as outlined above for the second reaction zone product stream 213.

In the embodiment depicted in FIG. 2, the second water removal zone product stream 214 is introduced to a separator 205 where the desired product, such as, for example, C$_2$ to C$_5$ hydrocarbons are separated from the remainder of the components in the second water removal zone product stream 214. The isolated, desired product is removed from the separator 205 as a product stream 215 comprising hydrocarbons. The remainder of the components of the second water removal zone product stream 214 (e.g., H$_2$ and CO) are removed from the separator 205 as a recycle stream 220 and combined with the feed stream 222 and the first water removal zone product stream 221. It should be understood that any suitable separation process may be used to separate the desired product, such as C$_2$ to C$_5$ hydrocarbons, from the remainder of the components in the second water removal zone product stream 214. In embodiments, the separator 205 may comprise separation processes as discussed above regarding separator 106 in FIG. 1.

It should be understood that in the embodiment depicted in FIG. 2, a heater or cooler may optionally be placed before any of the reaction zones, water removal zones, or the separator to heat or cool the streams entering any of the reaction zones, water removal zones, or the separator to the desired temperature for the processes taking place in the reaction zones, water removal zones, or the separator. The type of heater or cooler used is not limited so long as it is capable of heating or cooling the incoming product stream to the desired process temperature.

Additional systems and processes for preparing C$_2$ to C$_5$ hydrocarbons according to embodiments will now be described with reference to FIG. 3. The embodiment of a system for preparing C$_2$ to C$_5$ hydrocarbons 300 depicted in FIG. 3 includes four distinct reaction zones; a first reaction zone 301, a second reaction zone 302, a third reaction zone 304, and a fourth reaction zone 305. Between the second reaction zone 302 and the third reaction zone 304 is a first water removal zone 303, a second water removal zone 306 is fluidly connected to the fourth reaction zone 305 and a separator 307. The reaction zones 301, 302, 304, and 305, the water removal zones 303 and 306, and the separator 307 are fluidly connected to adjacent zones. For example, the first reaction zone 301 is fluidly connected to the second reaction zone 302, and the second reaction zone 302 is fluidly connected to the first water removal zone 303. The first water removal zone 303 is fluidly connected to a third reaction zone 304, and the third reaction zone 304 is fluidly connected to the fourth reaction zone 305. The fourth reaction zone 305 is fluidly connected to the second water removal zone 306. The second water removal zone 306 is fluidly connected to a separator 307, and the separator 307 is fluidly connected to the first reaction zone 301. The separator separates the desired product from the other components of an input stream, thereby isolating the desired product and providing the other components as a recycle stream.

In embodiments, the first reaction zone 301 may be a hybrid reactor that comprises a hybrid catalyst. The hybrid catalyst may include: (1) a methanol synthesis component; and (2) a solid microporous acid component having 8-MR access. In some embodiments, the methanol synthesis component is selected from the group consisting of a copper oxide catalyst, a copper oxide/zinc oxide catalyst, a copper oxide/alumina catalyst, a copper oxide/zinc oxide/alumina catalyst, a chromium oxide/zinc oxide catalyst, and combinations thereof. In embodiments, the solid microporous acid component is selected from molecular sieves having 8-MR access to limit the size distribution of products and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the molecular sieve may be SAPO-34 silicoaluminophosphate having a CHA framework type. It should be understood that the hybrid reactor of the first reaction zone 301 may be the same as the hybrid reactors described above with reference to the embodiments of FIG. 1 and FIG. 2.

In some embodiments, the second reaction zone 302 may include a R-WGS reactor. In the R-WGS reactor, $CO_2$ and $H_2$ from a feed stream are converted to CO and water. The second reactor zone operates at temperatures from greater than or equal to 300° C. to less than or equal to 750° C., from greater than or equal to 380° C. to less than or equal to 650° C., or about 500° C., and pressures from greater than or equal to 10 bar (1000 kPa) to less than or equal to 100 bar (10000 kPa), such as from greater than or equal to 25 bar (2500 kPa) to less than or equal to 75 bar (7500 kPa), or from greater than or equal to 35 bar (3500 kPa) to less than or equal to 65 bar (6500 kPa). It should be understood that the R-WGS reactor may be the same as the R-WGS reactor described above with reference to the embodiment of FIG. 2.

In further embodiments, the water removal zone 303 may include any suitable reaction or process for removing water from a gas stream, such as, for example, condensing by cooling, using a membrane that separates water from the gas stream, or adding a water absorbent to remove water from the gas stream. By removing water from the gas stream between each reaction zone, the carbon feed stream going into subsequent reaction zones is essentially water free, which permits higher conversion of the carbon in the carbon feed stream to desired products, such as $C_2$ to $C_5$ hydrocarbons. It should be understood that the water removal zone 303 may be the same as the water removal zones described above with reference to the embodiment of FIG. 1 and FIG. 2.

Referring again to FIG. 3, the third reaction zone 304 may be a hybrid reactor that comprises a hybrid catalyst. The hybrid catalyst may include: (1) a methanol synthesis component; and (2) a solid microporous acid component having 8-MR access. In some embodiments, the methanol synthesis component is selected from the group consisting of a copper oxide catalyst, a copper oxide/zinc oxide catalyst, a copper oxide/alumina catalyst, a copper oxide/zinc oxide/alumina catalyst, a chromium oxide/zinc oxide catalyst, and combinations thereof. In embodiments, the solid microporous acid component is selected molecular sieves having 8-MR access to limit the size distribution of products and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the molecular sieve may be SAPO-34 silicoaluminophosphate having a CHA framework type. It should be understood that the hybrid reactor of the third reaction zone 304 may be the same as the hybrid reactors described above with reference to the embodiments of FIG. 1 and FIG. 2.

In embodiments, the fourth reaction zone 305 may include a R-WGS reactor. In the R-WGS reactor, $CO_2$ and $H_2$ from a feed stream are converted to CO and water. The fourth reactor zone operates at temperatures from greater than or equal to 300° C. to less than or equal to 750° C., from greater than or equal to 380° C. to less than or equal to 650° C., or about 500° C., and pressures from greater than or equal to 10 bar (1000 kPa) to less than or equal to 100 bar (10000 kPa), such as from greater than or equal to 25 bar (2500 kPa) to less than or equal to 75 bar (7500 kPa), or from greater than or equal to 35 bar (3500 kPa) to less than or equal to 65 bar (6500 kPa). It should be understood that the R-WGS reactor may be the same as the R-WGS reactor described above with reference to the embodiment of FIG. 2.

In other embodiments, the second water removal zone 306 may include any suitable reaction or process for removing water from a gas stream, such as, for example, condensing by cooling, using a membrane that separates water from the gas stream, or adding a water absorbent to remove water from the gas stream. By removing water from the gas stream between each reaction zone, the carbon feed stream going into subsequent reaction zones is essentially water free, which permits higher conversion of the carbon in the carbon feed stream to desired products, such as $C_2$ to $C_5$ hydrocarbons. It should be understood that the second water removal zone 306 may be the same as the first water removal zone 303 discussed above and/or the water removal zones described above with reference to the embodiment of FIG. 1 and FIG. 2.

In additional embodiments, any suitable reaction or process for separating the desired product from the other components in the feed stream may be used in the separator 307. It should be understood that in some embodiments, the separator 307 may comprise only one separation process, but in other embodiments, the separator 307 may include a plurality of separation processes. In embodiments, the separation processes that may occur in the separator 307 include: (1) bulk removal of water using condensation at low temperatures (such as the processes discussed above for the water removal zones); (2) $CO_2$ removal using a chemical adsorption system, such as, for example, a methylamine in water system that operates at temperatures from greater than or equal to 25° C. to less than or equal to 65° C., such as from greater than or equal to 35° C. to less than or equal to 55° C. and operates at pressures from greater than or equal to 8 bar (800 kPa) to less than or equal to 50 bar (5000 kPa), such as from greater than or equal to 15 bar (1500 kPa) to less than or equal to 35 bar (3500 kPa); (3) trace removal of water using a 3A molecular sieve at ambient temperature, such as from greater than or equal to 5° C. to less than or equal to 50° C., or from greater than or equal to 15° C. to less than or equal to 25° C. and pressures from greater than or equal to 8 bar (800 kPa) to less than or equal to 50 bar (5000 kPa), such as from greater than or equal to 15 bar (1500 kPa) to less than or equal to 35 bar (3500 kPa); (4) cryogenic separation of non-condensable gasses such as $H_2$ and $N_2$; (5) distillation to remove CO and methane from the product stream, the distillation operating with temperatures at the top of the column of −90° C., and temperatures at the bottom of the column at 45° C. and operating at pressures of 30 bar (3000 kPa). It should be understood that in embodiments these separation processes may be duplicated any number of times in the separator 307 and can be used in any combination. It should be understood that any suitable reaction or process for separating the desired product from the other components in the feed stream may be used. It should be understood that separator 307 may be the same as separator described above with reference to the embodiment of FIG. 1 and FIG. 2.

Further embodiments of processes for preparing $C_2$ to $C_5$ hydrocarbons will now be described with reference to FIG. 3. A feed stream 310 is fed into the first reaction zone 301, the feed stream comprising $H_2$ and a carbon-containing gas selected from CO, $CO_2$, and combinations thereof. In some embodiments, the $H_2$ gas is present in the feed stream 310 in an amount of from 10 volume percent (vol %) to 90 vol %, based on combined volumes of the $H_2$ gas and the gas selected from CO, $CO_2$, and combinations thereof. The feed stream 310 is contacted with a hybrid catalyst in the first reaction zone 301. The hybrid catalyst comprises: (1) a methanol synthesis component; and (2) a solid microporous acid component having 8-MR access. In some embodiments, the methanol synthesis component is selected from the group consisting of a copper oxide catalyst, a copper oxide/zinc oxide catalyst, a copper oxide/alumina catalyst, a copper oxide/zinc oxide/alumina catalyst, a chromium oxide/zinc oxide catalyst, and combinations thereof. In embodiments, the solid microporous acid component is selected from molecular sieves having 8-MR access to limit the size distribution of products and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the molecular sieve may be SAPO-34 silicoaluminophosphate having a CHA framework type. The feed stream 310 is contacted with the hybrid catalyst in the first reaction zone 301 under reaction conditions sufficient to form a first reaction zone product stream 311. The reaction conditions comprising: (1) a temperature ranging from 300 degrees ° C. to 440° C., such as from 350° C. to 400° C., or from 365° C. to 385° C.; (2) a pressure of at least 1 bar (100 kPa), such as at least 2 bar (200 kPa), or at least 3 bar (300 kPa); and (3) a GHSV of at least 500 $h^{-1}$, such as at least 550 $h^{-1}$, or at least 600 $h^{-1}$. The first reaction zone product stream comprises CO, $H_2$, $CO_2$, water, and hydrocarbons. The first reaction zone 301 functions in the same manner as reaction zones 101, 103, 105, and 201 discussed above, thus the function of the first reaction zone and the product stream produced thereby is not discussed in such detail here.

The first reaction zone product stream 311 is then introduced into a second reaction zone 302. In embodiments, the second reaction zone 302 is a R-WGS reactor where the $CO_2$ and $H_2$ in the first reaction zone product stream 311 is converted to CO and water. The operating conditions of the second reaction zone 302 are provided above. The conversion in the second reaction zone 302 provides a second reaction zone product stream 312 that comprises CO, $H_2$, $CO_2$, water, and hydrocarbons, such as $C_2$ to $C_5$ hydrocarbons. This conversion of $CO_2$ into CO provides more feed CO that can be used to form hydrocarbons.

The second reaction zone product stream 312 is, in embodiments, introduced into the first water removal zone 303. In the first water removal zone 303, at least a portion of the water in the second reaction zone product stream 312 is removed and discarded as water stream 319. The water may be removed from the second reaction zone product stream 312 by any suitable process, such as condensation by cooling, using a membrane that separates the water from the remainder of the second reaction zone product stream 312, or by adding an absorbent to the second reaction zone product stream 312. Processing conditions of the first water removal zone are discussed above. Removal of the water produces a first water removal zone product stream 313 that comprises $H_2$, CO, $CO_2$, and hydrocarbons. The hydrocarbons from the second reaction zone product stream 312 essentially pass through the first water removal zone 303, thus the hydrocarbons in the first water removal zone product stream 313 may comprise the same hydrocarbon components as outlined above for the second reaction zone product stream 312.

Figure 3:
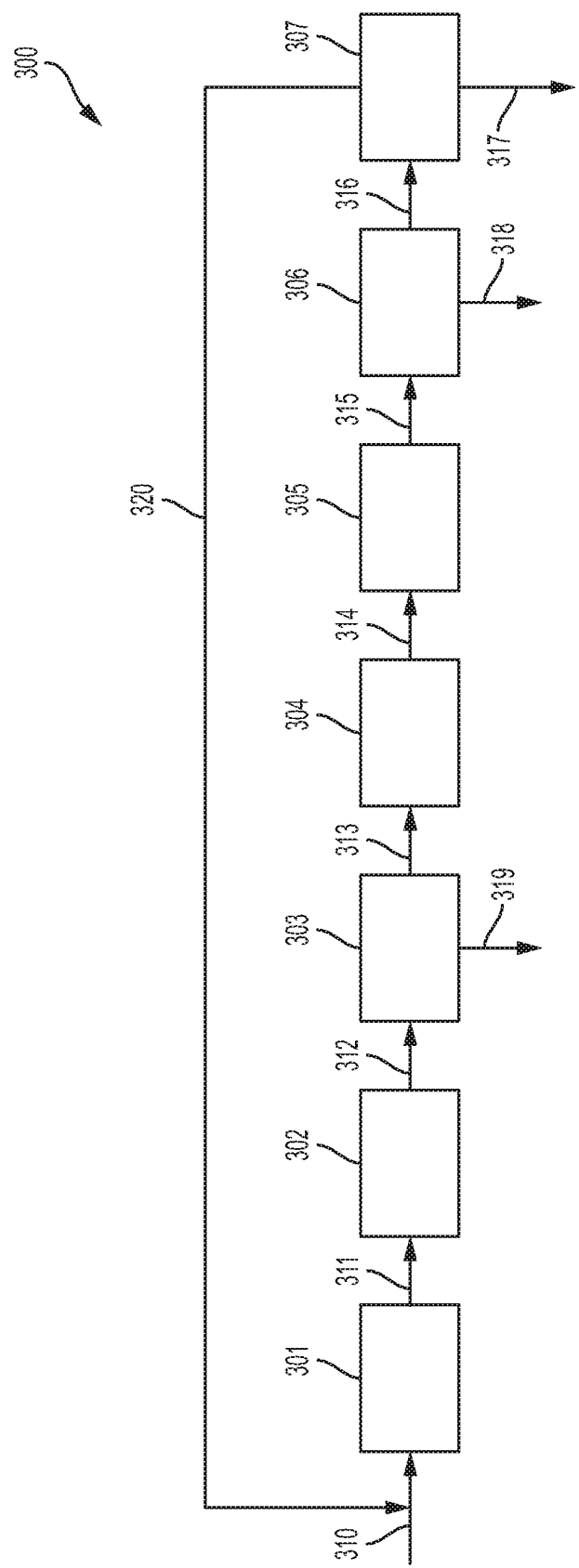
FIG. 3 is a block diagram flow chart for systems and processes of preparing $C_2$ to $C_5$ hydrocarbons according to embodiments disclosed and described herein.

With reference to embodiments shown in FIG. 3, the first water removal zone product stream 313 is introduced into the third reaction zone 304. The third reaction zone 304, may comprise a hybrid catalyst as disclosed for the first reaction zone 301 above, and the third reaction zone 304 may function in the same manner as the first reaction zone 301. After the first water removal zone product stream 313 is contacted with the hybrid catalyst at the process conditions for a hybrid catalyst disclosed above, a third reaction zone product stream 314 exits the third reaction zone 304.

The third reaction zone product stream 314 is introduced into fourth reaction zone 305. The fourth reaction zone 305 is, in embodiments, a R-WGS reactor where the $CO_2$ and $H_2$ in the third reaction zone product stream 314 is converted to CO and water. The operating conditions of the fourth reaction zone 305 are provided above. The conversion in the fourth reaction zone 305 provides a fourth reaction zone product stream 315 that comprises CO, $H_2$, $CO_2$, water, and hydrocarbons, such as $C_2$ to $C_5$ hydrocarbons. This conversion of $CO_2$ into CO provides more feed CO that can be used to form hydrocarbons.

As shown in the embodiments of FIG. 3, the fourth reaction zone product stream 315 is introduced to the second water removal zone 306. In the second water removal zone 306, at least a portion of the water in the fourth reaction zone product stream 315 is removed and discarded as water stream 318. The water may be removed from the fourth reaction zone product stream 315 by any suitable process, such as condensation by cooling, using a membrane that separates the water from the remainder of the fourth reaction zone product stream 315, or by adding an absorbent to the fourth reaction zone product stream 315. Processing conditions of the second water removal zone are discussed above. Removal of the water produces a second water removal zone product stream 316 that comprises $H_2$, CO, $CO_2$, and hydrocarbons. The hydrocarbons from the fourth reaction zone product stream 315 essentially pass through the second water removal zone 306, thus the hydrocarbons in the second water removal zone product stream 316 may comprise the same hydrocarbon components as outlined above for the fourth reaction zone product stream 315.

In the embodiment depicted in FIG. 3, the second water removal zone product stream 316 is introduced to a separator 307 where the desired product, such as, for example, $C_2$ to $C_5$ hydrocarbons are separated from the remainder of the components in the second water removal zone product stream 316. The isolated, desired product is removed from the separator 307 as a product stream 317 comprising hydrocarbons. The remainder of the components of the second water removal zone product stream 316 (e.g., $H_2$ and CO) are removed from the separator 307 as a recycle stream 320 and combined with the feed stream 310. It should be understood that any suitable separation process may be used to separate the desired product, such as $C_2$ to $C_5$ hydrocarbons, from the remainder of the components in the second water removal zone product stream 316. In embodiments, the separator 307 may comprise separation processes as discussed above regarding separator 106 in FIG. 1 and separator 205 in FIG. 2.

It should be understood that in the embodiment depicted in FIG. 3, a heater or cooler may optionally be placed before any of the reaction zones, water removal zones, or the separator to heat or cool the streams entering any of the reaction zones, water removal zones, or the separator to the desired temperature for the processes taking place in the reaction zones, water removal zones, or the separator. The type of heater or cooler used is not limited so long as it is capable of heating or cooling the incoming product stream to the desired process temperature. It should also be understood that although FIG. 3 depicts two hybrid reaction zones, two R-WGS reaction zones, and two water removal zones, any desirable number of these zones may be utilized to drive the reactions to completion and provide a desired product stream.

EXAMPLES

Embodiments will be further clarified by the following examples.

Example 1

Experiment A

One gram of a copper-zinc-aluminum methanol synthesis component (HiFUEL™ R120, manufactured by Alfa Aesar™, a Johnson Matthey Company) was mixed with 0.33 grams of a silicoaluminophosphate catalyst (SAPO-34) by shaking them together in a bottle. Each of the catalysts had a particle size before mixing within a range of from 40 mesh (0.422 millimeter) to 80 mesh (0.178 millimeter). The catalyst was loaded in a single reactor. The SAPO-34 was prepared in the following way. A reaction mixture was prepared by combining: 8.2 grams of aluminum isopropoxide ($Al(OC_3H_7)_3$) with a solution of 3.9 grams of 85 wt. % orthophosphoric acid in 8.4 grams of water, while stirring. To this mixture were added: 1.2 grams of an aqueous sol of 30 wt. % $SiO_2$ (Ludox AS-30) and 0.5 grams of water, and the mixture stirred until homogeneous. To this mixture was added: 16.8 grams of an aqueous solution of 35 wt. % tetraethylammonium hydroxide (TEAOH). Synthesis Conditions for the SAPO-34 were: placing the reaction mixture in a stainless steel stirred Parr reactor and heated to 200° C. at 0.5° C./min. The temperature was maintained for 120 hours under autogenous pressure while stirring at 60 RPM. The product was recovered by centrifugation, washed with water and dried at 90° C. overnight.

Experiment B

A mixture of 0.3333 grams of a copper-zinc-aluminum methanol synthesis component (HiFUEL™ R120) and 0.11 grams of a silicoaluminophosphate catalyst (SAPO-34) was made by shaking them together in a bottle. Each of the catalysts had a particle size before mixing within a range of from 40 mesh (0.422 millimeter) to 80 mesh (0.178 millimeter). The catalyst was loaded in a first reactor. This process was repeated for a second and third reactor. The three reactors were connected in series with the outlet stream of reactor 1 connected to the inlet of reactor 2 and the outlet stream of reactor 2 connected to the inlet of reactor 3. In between the reactors, the gas stream was sent through a knock-out vessel which removes the majority of the water from the gas stream before it enters the next reactor. The fixed bed reactor consists of a stainless steel (SS-316L) reactor tube with an outer diameter of ⅜" (9.525 mm) and a wall thickness of 0.035" (0.889 mm). The total reactor length is 384 mm. The exit line of the reactor is connected to a stainless steel (SS-316L) knock-out vessel. The exit line of the reactor acts as a dip-pipe that goes into the knock-out vessel. The knock-out vessel has a total length of 164 mm (including the connections at the top and bottom) and a volume of 95 ml. The knock-out vessel is kept at a temperature of 70° C. For a single-reactor experiment, the exit line coming from the knock-out vessel is directed to a GC for analysis. For a multi-reactor experiment, the exit line coming from the first knock-out vessel (which is connected to the first reactor) is connected to the inlet of the second reactor. Each reactor is connected to its own dedicated knock-out vessel. This sequence is repeated for all reactors. The exit line coming from the last knock-out vessel (attached to the last reactor) is directed to a GC for analysis.

Experiment C

This experiment is a duplicate of Experiment A, but used 3 grams of the copper-zinc-aluminum methanol synthesis component (HiFUEL™ R120) with 0.99 grams of a silicoaluminophosphate catalyst (SAPO-34) for the single reactor.

Experiment D

This experiment is a duplicate of Experiment B, but used 1 gram of a copper-zinc-aluminum methanol synthesis component (HiFUEL™ R120) with 0.33 grams of a silicoaluminophosphate catalyst (SAPO-34) per reactor.

For experiments A through D: the physically mixed catalyst was activated using a pure hydrogen stream at a flow of 100 ml/min, a temperature of 270° C. and at a pressure of 10 bars (1.0 MPa) for a period of 6 hours. The system was pressurized with pure nitrogen up to 50 bar (5.0 MPa). The system was heated to 390° C. while still flowing pure nitrogen. CO, $H_2$, and He were passed over the catalyst at the following flow rates: 22.5 ml/min CO; 67.5 ml/min $H_2$; and 10 ml/min He.

Figure 4:
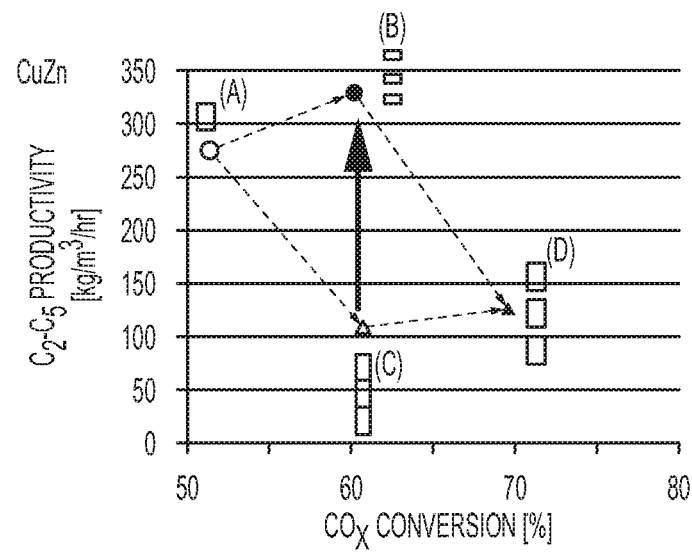
FIG. 4 is a graph of $C_2$ to $C_5$ productivity versus $CO_x$ conversion according to embodiments disclosed an described herein.

The results of this Example are shown in FIG. 4 and Table 1.

TABLE 1

| Experiment | GHSV (m³ gas/m³ catalyst overall/hr) | $CO_x$ Conversion (%) | $C_2$–$C_5$ Hydrocarbon Productivity (kg/m³ catalyst overall/hr) | $C_2$–$C_5$ Hydrocarbon Selectivity (%) | $CO_2$ Selectivity (%) |
|---|---|---|---|---|---|
| A | 3983 | 51.5 | 274 | 58.3 | 36.4 |
| B | 3983 | 60.3 | 327 | 64.6 | 28.0 |
| C | 1328 | 60.8 | 106 | 62.5 | 31.1 |
| D | 1328 | 69.7 | 124 | 67.5 | 21.1 |

Example 2

Experiment E

One gram of a chromium-zinc methanol synthesis component (Cr/Zn atomic ratio of 0.4/1) was mixed with 0.5 gram of a silicoaluminophosphate catalyst (SAPO-34) by shaking them together in a bottle. The chromium-zinc methanol synthesis component is made by targeting a Cr to Zn molar ratio of 0.4:1 (27 wt % $Cr_2O_3$ and 73 wt % ZnO). Appropriate quantities of $Cr(NO_3)_3.9H_2O$ and $Zn(NO_3)_2.3H_2O$ are added to distilled water ($H_2O$). In addition, a 0.5 M solution of $(NH_4)_2CO_3$ is prepared as a precipitating agent. The cation ($Cr^{3+}/Zn^{2+}$) and anion (($CO_3$)$^{2-}$) solutions are simultaneously added drop wise to a stirred beaker of distilled $H_2O$ maintained at 7.0<=pH<=7.5 and T=338+/−5 K. Co-precipitated materials are filtered, washed with distilled water, dried in static air at 393 K, and subsequently calcined at 873 K for 2 h. Each of the catalysts had a particle size before mixing within a range of from 40 mesh (0.422 millimeter) to 80 mesh (0.178 millimeter). The catalyst was loaded in a single reactor.

Experiment F

A mixture of 0.3333 grams of a chromium-zinc methanol synthesis component (Cr/Zn atomic ratio of 0.4/1) and 0.1666 grams of a silicoaluminophosphate catalyst (SAPO-34) was made by shaking them together in a bottle. Each of the catalysts had a particle size before mixing within a range of from 40 mesh (0.422 millimeter) to 80 mesh (0.178 millimeter). The catalyst was loaded in a first reactor. The previous process was repeated for a second and third reactor. The three reactors were connected in series with the outlet stream of reactor 1 connected to the inlet of reactor 2 and the outlet stream of reactor 2 connected to the inlet of reactor 3. In between the reactors, the gas stream was sent through a knock-out vessel which removes the majority of the water from the gas stream before it enters the next reactor. The reactors and knock-out vessels are the same as discussed above.

Experiment G

This experiment is a duplicate of Experiment E, but 3 grams of a chromium-zinc methanol synthesis component (Cr/Zn atomic ratio of 0.4/1) with 1.5 grams of a silicoaluminophosphate catalyst (SAPO-34) was used for the single reactor.

Experiment H

This experiment is a duplicate of Experiment F, but 1 gram of a chromium-zinc methanol synthesis component (Cr/Zn atomic ratio of 0.4/1) with 0.5 gram of a silicoaluminophosphate catalyst (SAPO-34) was used per reactor.

For experiments E through H: the physically mixed catalyst was activated using a gas stream consisting of 67 vol % hydrogen and 33 vol % nitrogen at a total flow rate of 33.75 ml/min, at a temperature of 400° C. and at atmospheric pressure (1 bar/0.1 MPa) for a period of 2 hours. The system was pressurized with pure nitrogen up to 50 bar (5.0 MPa). The temperature of the system was maintained at 400° C. CO, $H_2$, and He were passed over the catalyst at the following flow rates: 22.5 ml/min CO, 67.5 ml/min $H_2$ and 10 ml/min He The results as shown below in FIG. 5 and Table 2

TABLE 2

| Experiment | GHSV ($m^3$ gas/$m^3$ catalyst overall/hr) | $CO_x$ Conversion (%) | $C_2$—$C_5$ Hydrocarbon Productivity (kg/$m^3$ catalyst overall/hr) | $C_2$—$C_5$ Hydrocarbon Selectivity (%) | $CO_2$ Selectivity (%) |
|---|---|---|---|---|---|
| E | 2083 | 33.0 | 76 | 46.7 | 38.2 |
| F | 2083 | 34.6 | 79 | 47.4 | 35.7 |
| G | 680 | 50.6 | 41 | 52.0 | 34.7 |
| H | 680 | 56.9 | 46 | 58.9 | 27.9 |

Figure 5:
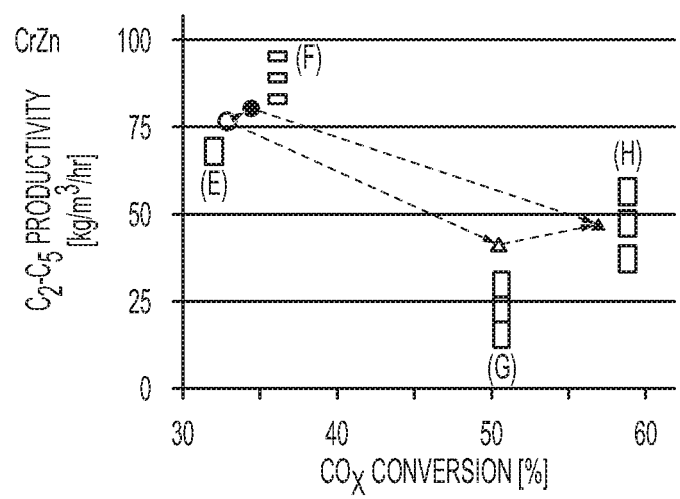
FIG. 5 is a graph of $C_2$ to $C_5$ productivity versus $CO_x$ conversion according to embodiments disclosed an described herein.

In FIGS. 4 and 5, the y-axis shows the $C_2$ to $C_5$ hydrocarbon productivity expressed in kg product per $m^3$ catalyst overall per hour. The x-axis shows the $CO_x$ conversion in % which is defined as:

$$CO_x \text{ conversion} = \frac{CO_{in} + CO_{2\,in} - CO_{out} - CO_{2\,out}}{CO_{in} + CO_{2\,in}} * 100\% \quad CO_X \text{ conversion} = \frac{CO_{in} + CO_{2_{in}} - CO_{out} - CO_{2_{out}}}{CO_{in} + CO_{2_{in}}} * 100\%$$

The $CO_x$ conversion displays the conversion of feed carbon (either from CO or from $CO_2$) to any product besides CO or $CO_2$. In other words, the conversion of CO to $CO_2$ or vice versa is excluded from this conversion number. The selectivities are expressed as carbon based selectivities reflecting the percentage of carbon exiting the reactor system in a particular product with respect to the total amount of carbon exiting the reactor system.

Examples 1 and 2 show that adding more catalyst for a 1 reactor system increases $CO_x$ conversion but also significantly lowers productivity; moving from a 1 reactor system to a staged reactor design with water removal increases both $CO_x$ conversion as well as productivity. At the same time, it results in a higher selectivity towards the desired product and in a lower selectivity towards (undesired) $CO_2$; and at equal $CO_x$ conversion, the staged reactor design with water removal results in higher catalyst productivity (up to 3 times higher for the CuO—ZnO/$Al_2O_3$+SAPO-34 hybrid catalyst, indicated by the arrow in FIG. 4).

Comparative Example 1

Physically mixed 1 gram of a copper-zinc-aluminum methanol synthesis component (HiFUEL™ R120) with 0.33 grams of a silicoaluminophosphate catalyst (SAPO-34) by shaking them together in a bottle. Each of the catalysts had a particle size before mixing within a range of from 40 mesh (0.422 millimeter) to 80 mesh (0.178 millimeter). The catalyst was loaded in a single reactor. The physically mixed catalyst was activated using a pure hydrogen stream at a flow of 100 ml/min, a temperature of 270° C., and a pressure of 10 bars (1.0 MPa) for a period of 6 hours. The system was pressurized with pure nitrogen up to 40 bar (4.0 MPa). The system was heated to 380° C. while still flowing pure nitrogen. CO, $CO_2$, $H_2$, and He were passed over the catalyst as indicated in Table 3 (experiments I through L).

Figure 6:
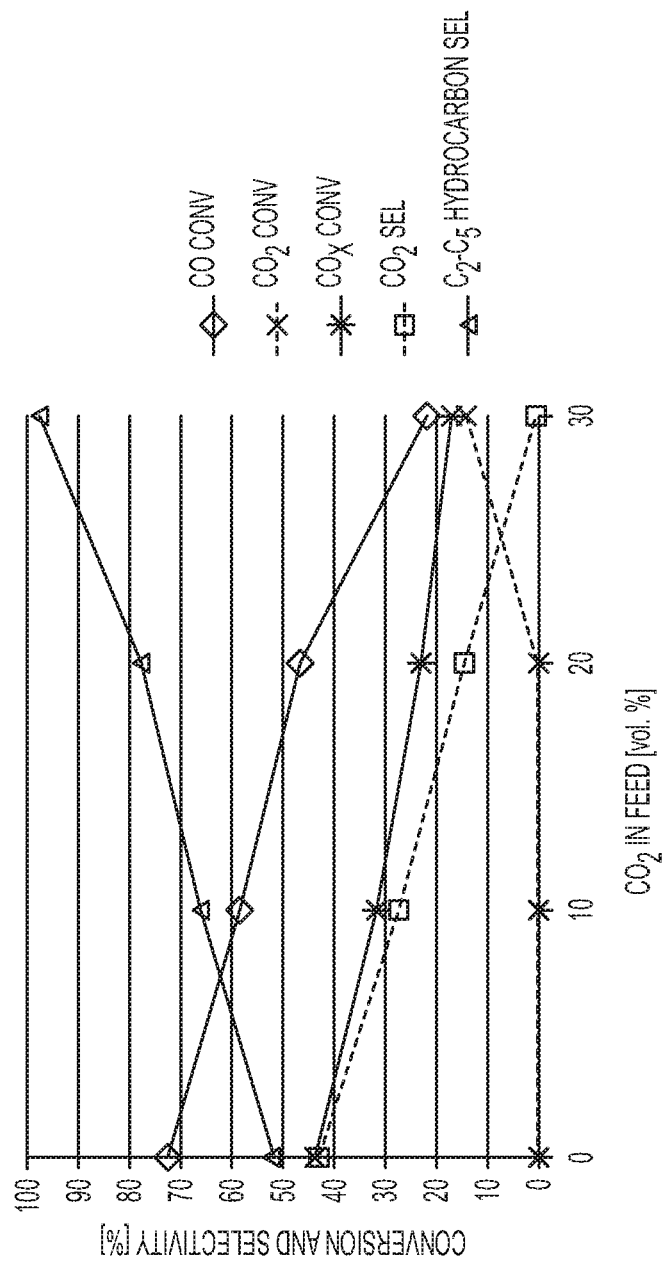
FIG. 6 is a graph of conversion and selectivity versus the concentration of $CO_2$ in the feed.

The results as shown below in FIG. 6 and Table 3.

TABLE 3

| Exp. | $CO_2$ Content (vol %) | CO Inlet Flow (sccm) | $CO_2$ Inlet Flow (sccm) | $H_2$ Inlet Flow (sccm) | He Inlet Flow (sccm) | $CO_x$ Conversion (%) | CO Conversion (%) | $C_2$-$C_5$ Hydrocarbon selectivity (%) | $CO_2$ Selectivity (%) |
|---|---|---|---|---|---|---|---|---|---|
| I | 0 | 22.5 | 0 | 67.5 | 5 | 43 | 72 | 52 | 43 |
| J | 10 | 21.0 | 10 | 63.0 | 5 | 31 | 58 | 66 | 27 |
| K | 20 | 19.0 | 20 | 57.0 | 5 | 22 | 46 | 77 | 14 |
| L | 30 | 16.5 | 30 | 49.5 | 5 | 16 | 21 | 97 | 0 |

The results of Comparative Example 1 show a reduction in $CO_x$ conversion with increasing $CO_2$ content in the feed.

Comparative Example 2

Experiment M

One gram of a copper-zinc-aluminum methanol synthesis component (HiFUEL™ R120) was mixed with 0.33 grams of a silicoaluminophosphate catalyst (SAPO-34) by shaking them together in a bottle. Each of the catalysts had a particle size before mixing within a range of from 40 mesh (0.422 millimeter) to 80 mesh (0.178 millimeter). The catalyst was loaded in a single reactor. The physically mixed catalyst was activated using a pure hydrogen stream at a flow of 100 ml/min, a temperature of 270° C. and a pressure of 10 bars (1.0 MPa) for a period of 6 hours. The system was pressurized with pure nitrogen up to 50 bar (5.0 MPa). The system was heated to 390° C. while still flowing pure nitrogen. CO, $H_2O(g)$, $H_2$, and $N_2$ were passed over the catalyst as indicated in Table 4 (experiments M-1 through M-5).

Experiment N

One gram of a chromium-zinc methanol synthesis component (Cr/Zn atomic ratio of 0.4/1) was mixed with 0.5 gram of a silicoaluminophosphate catalyst (SAPO-34) by shaking them together in a bottle. Each of the catalysts had a particle size before mixing within a range of from 40 mesh (0.422 millimeter) to 80 mesh (0.178 millimeter). The catalyst was loaded in a single reactor. The physically mixed catalyst was activated using a gas stream consisting of 67 vol % hydrogen and 33 vol % nitrogen at a total flow rate of 33.75 ml/min, at a temperature of 400° C., and at atmospheric pressure (1 bar/0.1 MPa) for a period of 2 hours. The system was pressurized with pure nitrogen up to 50 bar (5.0 MPa). The system was heated to 400° C. while still flowing pure nitrogen. CO, $H_2O(g)$, $H_2$, and $N_2$ were passed over the catalyst as indicated in Table 4 (experiments N-1 through N-5).

The results for experiments M and N are displayed in Table 4 below.

TABLE 4

| Experiment | $H_2O$ Content (vol %) | CO Inlet Flow (sccm) | $H_2O$ Inlet Flow (sccm) | $H_2$ Inlet Flow (sccm) | $N_2$ Inlet Flow (sccm) | $CO_x$ Conversion (%) | $C_2$-$C_5$ Hydrocarbon Selectivity (%) |
|---|---|---|---|---|---|---|---|
| M-1 | 0 | 22.5 | 0 | 67.5 | 10 | 49 | 59 |
| M-2 | 11 | 22.5 | 12 | 67.5 | 10 | 26 | 36 |
| M-3 | 16 | 22.5 | 19 | 67.5 | 10 | 6 | 8 |
| M-4 | 27 | 22.5 | 37 | 67.5 | 10 | 0 | 0 |
| M-5 | 43 | 22.5 | 75 | 67.5 | 10 | 0 | 0 |
| N-1 | 0 | 22.5 | 0 | 67.5 | 10 | 31 | 42 |
| N-2 | 12 | 22.5 | 13 | 67.5 | 10 | 17 | 20 |
| N-3 | 17 | 22.5 | 20 | 67.5 | 10 | 10 | 10 |
| N-4 | 21 | 22.5 | 27 | 67.5 | 10 | 4 | 2 |
| N-5 | 35 | 22.5 | 54 | 67.5 | 10 | 0 | 0 |

The (comparative) example shows a reduction in $CO_x$ conversion and $C_2$-$C_5$ hydrocarbon selectivity with increasing $H_2O$ content in the feed.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

The invention claimed is:

1. A process for preparing $C_2$ to $C_5$ hydrocarbons comprising:
   introducing a feed stream comprising hydrogen gas and a carbon-containing gas selected from the group consisting of carbon monoxide, carbon dioxide, and mixtures thereof into a first reaction zone;
   contacting the feed stream and a hybrid catalyst in the first reaction zone, wherein the hybrid catalyst comprises a methanol synthesis component and a microporous solid acid component, wherein the microporous solid acid component is a molecular sieve having 8-MR access;
   introducing a reaction zone product stream into a water removal zone that is downstream from the first reaction zone, wherein the water removal zone removes at least a portion of water from the reaction zone product stream; and
   introducing a product stream from the water removal zone into a second reaction zone, resulting in a final stream comprising $C_2$ to $C_5$ hydrocarbons.

2. The process for preparing $C_2$ to $C_5$ hydrocarbons according to claim 1, wherein the second reaction zone comprises a second hybrid catalyst, the second hybrid catalyst comprises a methanol synthesis component and a microporous solid acid component, wherein the microporous solid acid component is a molecular sieve having 8-MR access.

3. The process for preparing $C_2$ to $C_5$ hydrocarbons according to claim 1, wherein the second reaction zone is a reverse water gas shift reaction zone that reacts carbon dioxide and hydrogen in the reaction zone product stream and forms carbon monoxide and water.

4. The process for preparing $C_2$ to $C_5$ hydrocarbons according to claim 1, wherein the second reaction zone is positioned downstream from the first reaction zone, and a second water removal zone is positioned downstream from the second reaction zone.

5. The process for preparing $C_2$ to $C_5$ hydrocarbons according to claim 1, wherein a third reaction zone is positioned downstream from the first reaction zone, upstream from the water removal zone, and upstream from the second reaction zone, and
   the third reaction zone is a reverse water gas shift reaction zone that reacts carbon dioxide and hydrogen and forms carbon monoxide and water.

6. The process for preparing $C_2$ to $C_5$ hydrocarbons according to claim 1, wherein a fourth reaction zone is positioned downstream from the water removal zone and downstream from the second reaction zone, wherein the fourth reaction zone is a reverse water gas shift reaction zone that reacts carbon dioxide and hydrogen and forms carbon monoxide and water.

7. The process for preparing $C_2$ to $C_5$ hydrocarbons according to claim 1, wherein a product stream is introduced into a fifth reaction zone that is located downstream of the second reaction zone, wherein the fifth reaction zone includes a hybrid catalyst comprising a methanol synthesis component and a microporous solid acid component, wherein the microporous solid acid component is a molecular sieve having 8-MR access.

8. The process for preparing $C_2$ to $C_5$ hydrocarbons according to claim 1, wherein a final product stream comprising carbon monoxide, hydrogen, and hydrocarbons is introduced into a separation zone that is located downstream from the second reaction zone, wherein the separation zone separates the final product stream into a first product stream comprising hydrocarbons and a second product stream comprising carbon monoxide and hydrogen.

9. The process for preparing $C_2$ to $C_5$ hydrocarbons according to claim 8, wherein the second product stream is recycled by combining the second product stream and the feed stream.

10. The process for preparing $C_2$ to $C_5$ hydrocarbons according to claim 1, wherein the first reaction zone, the water removal zone, and the second reaction zone are stages within a single unit.

11. The process for preparing $C_2$ to $C_5$ hydrocarbons according to claim 1, wherein the first reaction zone, the water removal zone, and the second reaction zone are separate units.

12. The process for preparing $C_2$ to $C_5$ hydrocarbons according to claim 1, wherein the first reaction zone is operated at reaction conditions sufficient to form a first reaction zone product stream, the reaction conditions comprising:
a reaction temperature ranging from greater than or equal to 300° C. to less than or equal to 440° C.;
a reaction pressure of at least one bar (100 kPa); and
a gas hourly space velocity of at least 500 reciprocal hours.

13. The process for preparing $C_2$ to $C_5$ hydrocarbons according to claim 2, wherein the second reaction zone is positioned downstream from the first reaction zone, and a second water removal zone is positioned downstream from the second reaction zone.

14. The process for preparing $C_2$ to $C_5$ hydrocarbons according to claim 3, wherein the second reaction zone is positioned downstream from the first reaction zone, and a second water removal zone is positioned downstream from the second reaction zone.

15. The process for preparing $C_2$ to $C_5$ hydrocarbons according to claim 2, wherein a third reaction zone is positioned downstream from the first reaction zone, upstream from the water removal zone, and upstream from the second reaction zone, and
the third reaction zone is a reverse water gas shift reaction zone that reacts carbon dioxide and hydrogen and forms carbon monoxide and water.

16. The process for preparing $C_2$ to $C_5$ hydrocarbons according to claim 3, wherein a third reaction zone is positioned downstream from the first reaction zone, upstream from the water removal zone, and upstream from the second reaction zone, and
the third reaction zone is a reverse water gas shift reaction zone that reacts carbon dioxide and hydrogen and forms carbon monoxide and water.

* * * * *